United States Patent [19]

Mosmann

[11] Patent Number: 4,690,893

[45] Date of Patent: Sep. 1, 1987

[54] HYBRIDOMA CELL LINES PRODUCING MONOCLONAL ANTIBODIES WHICH SPECIFICALLY BIND TO MOUSE INTERLEUKIN-2

[75] Inventor: Tim R. Mosmann, Atherton, Calif.

[73] Assignee: DNAX Research Institute of Molecular and Cellular Biology, Inc., Palo Alto, Calif.

[21] Appl. No.: 730,308

[22] Filed: May 3, 1985

[51] Int. Cl.$^4$ .......................... C12N 5/00; C07K 15/04

[52] U.S. Cl. .............................. 435/240.27; 530/387; 435/68; 435/70; 435/172.2; 435/241; 435/948; 435/172.3; 435/317; 935/103; 935/108; 935/110

[58] Field of Search ................ 435/68, 70, 172.2, 241, 435/240, 948, 172.3, 317; 935/89, 90, 92, 93, 95, 102, 103, 104, 106, 108, 110; 260/112 R; 530/387, 388

[56] References Cited

U.S. PATENT DOCUMENTS

| | | | |
|---|---|---|---|
| 4,196,265 | 4/1980 | Koprowski | 435/68 |
| 4,390,623 | 6/1983 | Frabricius | 435/68 |
| 4,401,756 | 8/1983 | Gillis | 435/240 |
| 4,404,280 | 9/1983 | Gillis | 435/68 |
| 4,407,945 | 10/1983 | Gillis | 435/68 |
| 4,411,992 | 10/1983 | Gillis | 435/240 |
| 4,411,993 | 10/1983 | Gillis | 435/68 |
| 4,438,032 | 3/1984 | Golde et al. | 435/68 |
| 4,444,887 | 4/1984 | Hoffmann | 435/68 |
| 4,448,879 | 5/1984 | Fabricius et al. | 435/68 |
| 4,473,493 | 9/1984 | Gillis | 435/240 |
| 4,473,642 | 9/1984 | Gillis | 435/68 |
| 4,490,289 | 12/1984 | Stern | 435/68 |
| 4,517,293 | 5/1985 | Fabricius | 435/68 |

OTHER PUBLICATIONS

Lachman, L. B., Lymphokine Research, vol. 2(1), pp. 37–41 (1983), See p. 40.

Gillie, S., Federation Proceedings, FASEB, vol. 42, (9), pp. 2635–2638, (6–1983).

Staddler, B. M. et al, Federation Proceedings, FASEB, vol. 40 (3), p. 1111, abstract 5002 (3–1–1981).

Kern, D. E. et al, The Journal of Immunology, vol. 127, (4), pp. 1323–1328 (10–1981).

Stadler, B. M. et al, The Journal of Immunology, vol. 128 (4), pp. 1620–1624 (1982).

Gillis, S. et al., The Journal of Immunology, vol. 126(5), pp. 1978–1984 (5–1981).

Stull, D. et al, The Journal of Immunology, vol. 12615), pp. 1680–1683 (5–1981).

Harwell, L. et al, Journal of Experimental Medicine, vol. 152(4), pp. 893–904 (1980).

Stadler, B. M. et al, *Lymphokines and Thymic Hormones*, Goldstein, A. L. et al, eds, Raven Press, N.Y. (1981), pp. 69–73.

Stadler, B. M. et al, *Lympholcines*, vol. 6, pp. 117–135, Academic Press (1982).

*Primary Examiner*—Margaret Moskowitz

*Attorney, Agent, or Firm*—William M. Smith; Stephen C. Macevicz

[57] ABSTRACT

A hybridoma for production of monoclonal antibodies specific for mouse interleukin-2, but which antibodies do not significantly cross-react with human or rat interleukin-2. The hybridoma is a fusion product of a mouse myeloma cell line and from a rat immunized with supernatant from a mouse T cell line.

2 Claims, 2 Drawing Figures

HYBRIDOMA CELL LINES PRODUCING MONOCLONAL ANTIBODIES WHICH SPECIFICALLY BIND TO MOUSE INTERLEUKIN-2

FIELD OF THE INVENTION

The present invention relates basically to the development of hybridoma cell lines capable of secreting immunoglobulins reactive with mouse interleukin-2 ("IL-2") and, more particularly, to the production of monoclonal antibodies that are specific for mouse IL-2 but exhibit minimal cross-reactivity to native IL-2 from some other mammalian species (e.g., rat or human).

BACKGROUND OF THE INVENTION

The term "Monoclonal Antibodies" refers generally to a substantially homogeneous immunoglobulin population of a defined specificity that is produced by a cloned cell line. Although immunologists had isolated many plasmacytomas producing such immunoglobulins, it was not until the seminal work of Kohler and Milstein that the construction of cell lines secreting homogeneous antibodies of predetermined specificity against an antigen became feasible (Kohler, G. and Milstein, C., Nature 256: 495–497 [1975]).

Briefly, Kohler and Milstein's original experiments utilized Sendai virus to fuse a HAT (hypoxanthine, aminopterin and thymidine)-sensitive variant of a mouse myeloma cell line and spleen cells from mice immunized against sheep red blood cells. When cultured on HAT medium for about one week, only hybrid cells (fusions of the myeloma and spleen cells) survived—the myeloma cells died because of their HAT sensitivity, while the remaining normal spleen cells generally are unable to survive in culture. These hybrid cells, known as hybridomas, contained the HGPRT (hypoxanthine guanine phosphoribosyl transferase) salvage mechanism from normal cells needed to survive in HAT medium, yet retained the immortality capability of the myeloma fusion partner. Moreover, when separated out into individual cell clones, it was discovered that some of the hybridomas secreted large quantities of homogeneous antibodies specific for sheep red blood cells. Thus, a simple and effective method of producing monoclonal antibodies was realized.

Later, the easier and safer polyethylene glycol fusion treatment was substituted for the viral fusion (Ringerty, N. and Savage, R. Cell Hybrids, Academic Press, New York [1976]) and now it is the primary fusion mechanism utilized (Galfre, G. and Milstein, C. Meth. Enzym. 73: 3–46 [1981]). Otherwise, the Kohler and Milstein technique remains essentially unchanged.

The technique found rapid and universal acceptance in the scientific community, and a variety of hybridomas producing monoclonal antibodies of various specificities have been produced. In fact, the strategies for hybridoma production,—including choice of antigen, fusion partner cell and subsequent cultivation—are legion. (See generally, Golding, J., *Monoclonal Antibodies: Principles and Practice*, Academic Press, New York [1983]). However, the production of a hybridoma capable of secreting monoclonal antibodies having a precise range of binding properties (e.g., specific for a mammalian protein but not for the same protein from other species—although the protein may be very similar structurally between species) remains a very difficult problem, and one often resolved only fortuitously.

Monoclonal antibodies find utility in a vast number of ways, including: immunoassays, immunohistochemical staining, immunoabsorbent, and cell sorting procedures. Moreover, when specific for a protein (or some other molecule having a measurable activity on cells), the monoclonal antibody can be used to ascertain the molecule's function by determining the effect of antibody-mediated removal on the cellular system under experimentation.

With the advent of recombinant DNA technology, monoclonal antibodies have added utility as aids in immunochemical blotting—the so-called "Western Blots". The antibodies are used to detect the production of exogenous proteins, such as hormones on electrophoresed gels.

One hormone that has attracted considerable attention recently is interleukin-2 (IL-2), originally known as T cell growth factor. This lymphokine was discovered just over 10 years ago (Smith, K. Immunol. Rev. 51: 337–357 [1980]), and its prime function is almost certainly the stimulation and maintenance of proliferation of T cells—cells crucial in the mammalian immune response. In fact, the removal of IL-2 from proliferating T cells results in their death within a few hours (Ruscetti; F. et al., J. Immunol. 123: 2928–2931 [1977]). Thus, some immunologists believe that IL-2 may be at the center of the entire immune response. For a detailed review of IL-2 activities, see Farrar, J. et al., Immunol. Rev. 63: 129–166 [1982], which is incorporated herein by reference.

Not surprisingly, researchers have applied monoclonal antibody technology in an attempt to develop a better understanding of IL-2's role in the imune response, such as by developing better methods for its assay and purification. By way of example, at least three European Patent Application (Nos. 82302231.4, 83108444.7, and 83112532.3) have been published concerning monoclonal antibodies capable of binding IL-2, and at least one commercial source also exists (DMS-1; Genzyme Corporation, Boston, MA).

Each of these monoclonal antibodies reportedly exhibits significant binding affinity for human IL-2, and some also exhibit cross-reactivity with mouse and/or rat IL-2. While affinity for human IL-2 is very important for many purposes, it would be useful to have a monoclonal antibody that recognizes an epitope (an antigenic site) on mouse IL-2 that does not exist on human or rat IL-2. This would permit the determination (serologically or otherwise) of mouse IL-2 in the presence of human IL-2. Also, purification of mouse IL-2 and two site immunoassays become more feasible. Moreover, this would allow the experimental suppression of endogenous IL-2 (e.g., mouse), while adding an endogenous source (e.g., human or rat)—expanding immunologists' knowledge base concerning IL-2's role in the mammalian immune response.

Thus, there exists a need for a hybridoma capable of producing a monoclonal antibody specific for mouse IL-2, but which does not significantly cross-react with human or rat IL-2. The present invention fulfills this need.

SUMMARY OF THE INVENTION

The present invention provides hybrid cell lines that produce monoclonal antibodies specific for mouse interleukin-2 (IL-2), but which antibodies do not significantly cross-react to native IL-2 from other mammalian species, such as human or rat. One hybridoma that secretes antibodies of the rat $IgG_{2a}$ subclass has been designated as S4B6, and samples deposited with the American Type Culture Collection, 12301 Parklawn Drive, Rockville, Md., U.S.A. 20852, under accession number HB-8794.

In the process of the present invention, monoclonal antibodies specific for mouse IL-2 are made by: fusing an anti-mouse IL-2 antibody-producing cell and a fusion partner cell to form a hybridoma; propagating the hybridoma and collecting antibodies produced by the hybridoma, wherein said antibodies are not substantially cross-reactive with native IL-2 of other mammalian species. The antibody-producing cell may be obtained from spleen cells or lymph node cells of an animal, preferably a rat, immunized with mouse IL-2 or a fragment thereof comprised of an amino acid sequence unique to mouse IL-2 with respect to human and rat IL-2.

The hybridoma may be cultivated in vitro, such as in tissue culture, or in vivo, such as in the peritoneal cavities of mice. The fusion partner may have originated from a different species than the antibody-producing cell. For example, when the antibody-producing cell is a rat B lymphocyte, the fusion partner can be a mouse myeloma cell.

More specifically, a preferred embodiment of the present invention is a hybridoma capable of producing a monoclonal antibody which binds to unglycosylated or naturally glycosylated mouse IL-2, but which does not significantly bind to native IL-2 from human or rat sources. The hybridoma can be prepared by a method comprising the steps of: immunizing a rat with supernatant from a cell line producing mouse IL-2; removing B lymphocytes from the rat; fusing the B lymphocytes with a first mouse hybrid cell line to form second cell hybrids; selecting and cloning by limiting dilution individual cell hybrids to screen for and isolate a cell hybrid producing antibody specific for mouse IL-2; and assaying for cross-reactivity to rat and human native IL-2 to locate said hybridoma.

Other features and advantages of the present invention will become apparent from the following more detailed description, which describes the invention by way of example.

DESCRIPTION OF THE SPECIFIC EMBODIMENTS

Figure 1:
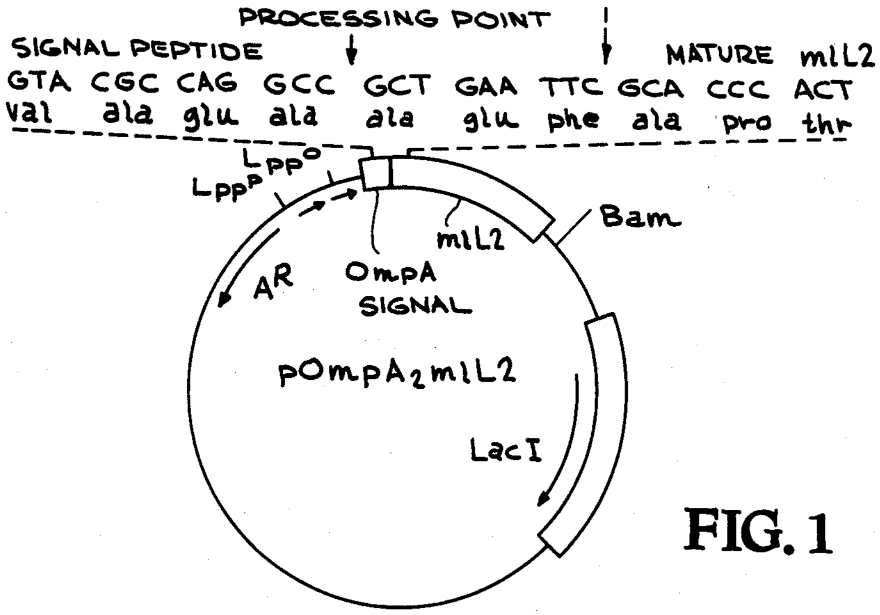
FIG. 1 illustrates pOmp $A_2$ mIL-2, a plasmid carrying a cDNA clone encoding mature mouse IL-2 activity and fused to the outer membrane protein A signal peptide.

In accordance with the present invention, hybridomas are provided that secrete monoclonal antibodies specific for mouse IL-2, but which antibodies do not significantly react with IL-2 from rat or human sources. The hybridomas may be produced using unpurified supernatant as antigen and generally according to the method of Kohler and Milstein with polyethylene glycol as a fusion agent, as follows:

A. Immunization

A preferred antigen for mouse IL-2 is supernatant from a mouse T cell line; however, T lymphomas (Farrar, J. et al., J. Immunol. 125: 2555–2558 [1980]) or mouse IL-2 purified from other sources is suitable (see Granelli-Piperno, A. et al., J. Exp. Med. 154: 422–430 [1981]). Once purified, cleavage fragments of IL-2 may be prepared according to well known procedures, such as cyanogen bromide treatment or enzymatic cleavage (e.g., pepsin, trypsin, etc.). Also, a commonly assigned patent application, U.S. Ser. No. 658,183, filed Oct. 5, 1984, describes the cloning and expression of cDNA clones encoding polypeptides exhibiting mouse IL-2 activity. This application, which is incorporated herein by reference, provides means for the production of mouse IL-2 in exogenous hosts (including bacteria, yeast, and monkey cells) the supernatants of which are a suitable antigenic source. Sequence comparison with the cDNA clone encoding human IL-2 (Taniguchi, T. et al., Nature 302: 305–310 [1983]) can provide information on amino acid sequences unique to mouse that also can be synthesized and used for immunization.

Immunization protocols are well known and can vary considerably yet remain effective. For a water-soluble protein, such as mouse IL-2, the use of an adjuvant is usually necessary. Typically, Freund's complete adjuvant is used. Alternatively, the antigen may be precipitated on alum, and then admixed with killed *Bordetella pertussis* organism or keyhole limpet haemocyanin. The first injection of antigen is usually given in a highly aggregated form, with subsequent immunizations either soluble or aggregated.

The injections can be subcutaneous, intraperitoneal or intravascular. Typically, 1 to 50 micrograms are given in emulsions of 1–2 milliliters for a rat, and one tenth as much for mice. Thereafter, one to ten or more booster immunizations can be given at 2–8 week intervals, with the last preferably 2–4 days prior to removing either the spleen and/or the regional drainage lymph nodes and making a cellular suspension of antibody producing cells (e.g., primed B lymphocytes) for the fusion.

B. Fusion

Numerous cell lines exist that can be used as the fusion partner cell for the generation of the hybridomas of the present invention. Myelomas, especially those not producing their own immunoglobulin chains, are preferred, but many of the MOPC-21 variants are suitable and all are widely available. Also, other myeloma cell lines and hybrid cell lines can be used. The fusion partner is usually drug resistant with respect to 8-azaguanine and/or 6-thioguanine, typically lacking the HPGRT enzyme function and hence unable to grow in HAT medium.

The actual fusion is most often in the presence of polyethylene glycol (PEG) in the molecular weight range of about 1,000 to 10,000 daltons, commonly about 1,500 daltons, however, other concentrations, fusion promoters and methodologies are known and are acceptable. The PEG concentration should be from about 30 to 60% (g/l), preferably 35 to 40%, at a pH of between about 7.0 and 8.2, and the exposure time about 1 to 2 minutes at higher PEG concentration and longer (e.g., up to about 7 to 10 minutes) at lower concentrations. Thereafter, the cells are harvested by centrifugation and harvested.

C. Selection, Cloning and Screening

The cells are then diluted and cultured for a week or more in separate wells containing an appropriate selective medium that will inhibit the viability of non-fused fusion partners (usually, non-fused antibody producing cells will expire within about 7 days). The dilution can vary depending on the expected hybrid cell formation (usually about 1 per $10^6$), but preferably will be at a low (e.g., less than 1 and up to 4 or more) viable hybrid cells in each well.

After selection, the wells are screened for the presence of antibody capable of recognizing mouse IL-2 by any of a number of well-known procedures, such as solid-phase radioimmunoassay, bioassay; enzyme-linked immunosorbent assays, rosetting assays, blocking assays, etc. Thereafter, positive wells are plated out into individual cell colonies by limiting diluton. As necessary, feeder cells (e.g., thymocytes from an appropriate source) can be added. Recloning is almost always advisable to insure clonality. Cross-reactivity studies can also be performed at this time utilizing the above-mentioned procedures.

D. Scaleup

Once the desired hybridoma has been identified and isolated, the monoclonal antibodies can be produced in vitro in large quantities by culturing in a medium supplemented with necessary additions. Typical antibody levels in culture range from about 5 to 50 micrograms/milliliter, depending on the individual clone and cell density.

For large quantities of antibody, it is easier to grow up the hybridomas in vivo, as tumors in animals, the serum or ascites fluid of which can provide up to about 50 milligrams/milliliter of monoclonal antibodies. Usually, injection (preferably intraperitoneal) of about $10^6$ to $10^7$ histocompatible hybridoma cells into mice or rats will result in tumor formaton after a few weeks. The antibodies can then be collected and processed by well known methods. (See generally *Immunological Methods*, vols. I & II, eds. Lefkovits, I. and Pernis, B., Academic Press, New York, N.Y. [1979 & 1981]; and *Handbook of Experimental Immunology*, ed. Weir, D., Blackwell Scientific Publications, St. Louis, MO [1978], both of which are incorporated herein by reference.)

EXPERIMENTAL

EXAMPLE 1

The antigen was prepared by incubating cells from the murine helper T cell line LB2-1 (ATCC accession number CRL-8629) at a concentration of $5\times10^6$ per ml in RPMI 1640 medium (Gibco, Grand Island, NY) lacking serum but containing 0.05 mM 2-mercaptoethanol and 4 micrograms per ml Concanavalin A (Con A) (Calbiochem, La Jolla, CA). After 24 hours incubation at 37° C., the cells were removed by centrifugation and the supernatant proteins concentrated approximately 30-fold by filtration under pressure through an Amicon YM5 membrane (Danvers, MA). The resulting concentrate was mixed with complete Freund's adjuvant and injected i.p. into an adult Lewis rat. Six injections were given over a period of six months.

Three days after the final injection, the rat spleen was taken and the cells divided into three parts. $2\times10^8$ spleen cells were mixed with $4\times10^7$ Sp/2 mouse hybrid cells (Shulman, M. et al., Nature 276: 269–270 [1978]) and pelletted by centrifugation at 900×g for 7 minutes. The cells were resuspended in RPMI 1640 and repelleted. The pellet was then resuspended in 2 mls 40% (w/w) PEG (molecular weight 8,000), mixed, and repelletted by centrifugation for 6 minutes at 600×g. The supernatant was removed and the pellet resuspended in RPMI 1640 containing 20% fetal bovine serum (Gibco). The cells were again pelletted by centrifugation and resuspended in the same medium to which was added 0.1 mM hypoxanthine, 0.03 mM thymidine, 0.0005 mM amethopterin, 0.05 mg/ml gentamycin (Schering, Kenilworth, NJ), and 0.05 mM 2-mercaptoethanol (2ME). The cell suspension was dispensed into ten 96-well flat-bottomed trays and incubated at 37° C. After about 3 days, the medium was exchanged for fresh medium containing the same supplements except amethopterin.

The supernatants from all 960 wells were assayed by pooling in groups of five and then testing the resulting 192 samples for the ability to inhibit the IL-2 bioassay. 0.05 ml sample was mixed with 0.05 ml RPMI 1640 containing 10% fetal bovine serum, 2,000 mouse HT2 cells (Watson, J., J. Exp. Med. 150: 1510–1519 [1979]) and a source of IL-2 sufficient to induce maximal growth for 24 hours (supplied as a 0.4% dilution of the supernatant of Con A-stimulated LB2-1 cells prepared as above). The trays were incubated at 37° C. in 5% $CO_2$. After twenty hours, 0.01 ml of 5 mg/ml MTT (3-(4,5-dimthylthiazol-2-yl)-2,5-diphenyl tetrazolium bromide, Sigma Chemical Co., St. Louis, MO) in phosphate-buffered saline (PBS) was added to each culture. Four hours later, 0.15 ml of 0.04N HCl in isopropanol was added to each culture and thoroughly mixed. After a few minutes, the plates were read on a Dynatech MR580 Microelisa Auto Reader (Dynatech Instruments, Inc., Torrance, CA), at a wavelength of 570 nm (reference wavelength of 630 nm) and a calibration setting of 1.99. (See, Mosmann, T., J. Immunol. Meth. 65: 55–63 [1983].)

All wells but one showed growth of the HT2 cells, indicating that only one sample was capable of inhibiting the IL-2 assay. The five wells contributing to this sample were tested individually, and one well (S4B6) had strong inhibitory activity. The hybridoma cells from this well were recloned by limiting dilution and individual clones picked. One of these subclones was used for further work.

The generation time of S4B6 cells is approximately 20 hours, growing in RPMI 1640 containing 10% fetal bovine serum and 0.05 mM 2-mercaptoethanol. The cells secrete rat $IgG_{2a}$ subclass antibody for short periods into RPMI 1640 not containing serum or into the defined medium HB102 (Hana Media Inc., Berkeley, CA). The hybridoma grows as ascites in mice primed one week previously with 0.5 mls pristane and given 150–450R gamma irradiation immediately before the cells were injected i.p. (about $2\times10^6$/mouse).

EXAMPLE 2

Supernatant from S4B6 cultures was concentrated 100 fold using Amicon PM-30 filter membranes and this antibody preparation was titrated by doubling dilutions over 16 wells (0.05 ml each), in triplicate, in a 96 well tray. All wells then received 0.05 ml medium containing about 2,000 HT2 cells and a source of IL-2 sufficient to induce maximal growth for 24 hours (supplied as a $4\times10^{-4}$% dilution of a lysate of *E. coli* expressing a mouse IL-2 cDNA clone). After 24 hours, the plates were assayed by the MTT assay and the results shown in Table I below. Data are expressed as the percent inhibition of the signal given by the HT2 cells in the presence of IL-2, but the absence of antibody.

TABLE I

| Dilution of S4B6 Supernatant | % Inhibition |
| --- | --- |
| 1/16 | 99 |
| 1/32 | 100 |
| 1/64 | 100 |
| 1/128 | 102 |
| 1/256 | 102 |
| 1/512 | 96 |
| 1/1024 | 89 |
| 1/2048 | 69 |
| 1/4096 | 46 |
| 1/8192 | 26 |
| 1/16384 | 8 |
| 1/32768 | 3 |
| 1/65536 | −2 |

EXAMPLE 3

Supernatant from S4B6 cultures was tested at a final concentration of 12.5%, in triplicate, in a 96 well tray. All wells received about 2,000 HT2 cells and a source of IL-2 sufficient to induce maximal growth for 24 hours, in a final volume of 0.1 ml. After 24 hours, the plates were assayed by the MTT assay and the results are shown in Table II. Data are expressed as the percent inhibition of the signal given by the HT2 cells in the prescence of IL-2, but the absence of antibody.

TABLE II

| IL-2 Source | % Inhibition |
| --- | --- |
| LB2-1 mouse IL-2 | 85 |
| Cos mouse IL-2 | 71 |
| Cos human IL-2 | 9 |
| Yeast mouse IL-2 | 73 |
| E. coli mouse IL-2 | 70 |
| Rat IL-2 | 1 |

Legend to Table II
LB2-1 mouse IL-2 - Supernatant from Concanavalin A stimulated LB2-1 cells.
Cos mouse IL-2 - Supernatant from Cos monkey cells transfected with the cDNA clone for mouse IL2.
Cos human IL-2 - Supernatant from Cos monkey cells transfected with the cDNA clone for human IL2.
Yeast mouse IL-2 Yeast lysate from yeast cells expressing the cDNA clone for mouse IL2.
E. coli mouse IL-2 - Lysate from E. coli expressing the cDNA clone for mouse IL2 (containing 3 extra amino acids at the N—terminus).
Rat IL-2 Supernatant from Con A stimulated rat spleen cells.

EXAMPLE 4

A column was packed with 0.5 ml of Protein-A Sepharose (Sigma, St. Louis, MO) and washed with phosphate buffered saline (PBS). Goat anti-Rat IgG antiserum (0.2 ml) was then passed through the column, followed by 5 ml of S4B6 supernatant. After washing with PBS, an amount of LB2-1 supernatant containing 1,900 units of IL-2 was passed through the column. (One unit of IL-2 is defined as the amount of factor that produces an OD of 50% of the maximum level, using 2,000 HT-2 cells in 0.1 ml for 24 hours.) The amount of IL-2 passing through the column was measured by the bioassay on HT2 cells. No IL-2 was detectable in the assay (with a lower limit of detection of 10 units). Thus, greater than 99% of the bioactivity of the IL-2 was removed by the column containing bound S4B6 antibody.

EXAMPLE 5

Figure 2:
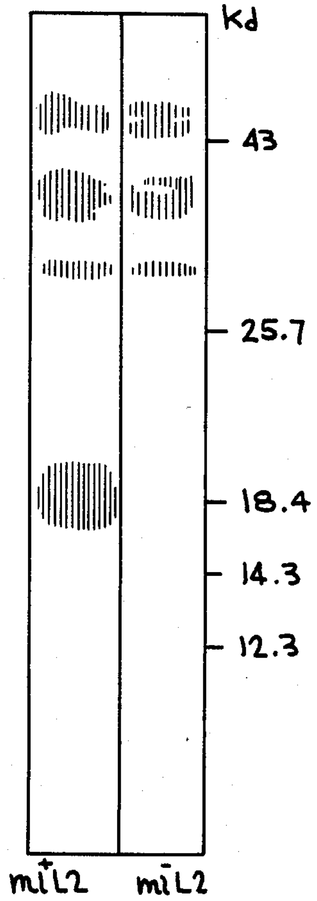
FIG. 2 is a Western Blot utilizing the monoclonal antibodies of the present invention and supernatant from a bacterial culture containing the plasmid depicted in FIG. 1 with (+) and without (−) the IL-2 cDNA insert.

The mouse IL-2 gene was expressed in E. coli using the secretion vector system developed J. Ghrayeb et al. (EMBO Journal 3: 2437-2442 [1984]). Using oligonucleotide-directed site-specific mutagenesis (Zoller, M. and Smith, M. Methods Enzymol. 101: 468-472 [1983]) an EcoR$_1$ restriction site (GAATTC) was inserted directly 5' to the mature mouse IL-2 sequence. Subsequently, the mature gene was isolated on a EcoR$_1$-BamH1 fragment and cloned into the E. coli secretion vector PIN-III-omPA2, as shown in FIG. 1, which was opened at its unique EcoR$_1$ and BamH sites. Transformants were grown for 5 hours at 37° C. Then, 200 µl cells were pelleted and resuspended in 50 µl SDS-gel sample buffer; and 10 µl samples were electrophoresed on a 15% SDS-polyacrylamide gel. After electrophoresis, the gel was transferred onto a piece of nitrocellulose paper by electrophoresis transfer (Burnette, W., "Western Blotting": Electrophoretic transfer of proteins from SDS-polyacrylamide gels to unmodified nitrocellulose and radiographic detection with antibody and radioiodinated protein A, Anal. Biochem. 112: 195-203 [1983]). The antibody of the present invention was added for two hours to bind with the protein. Then, $^{125}$I-labelled goat anti-rat Ig was added to bind the first antibody. Finally, the nitrocellulose paper was blotted dry and exposed at −70° C. to Kodak XR film. The results are shown in FIG. 2.

The results of the bioassay inhibition indicate that the monoclonal antibody produced by S4B6 can inhibit the activity of IL-2. This could be due to binding of the antibody to either the IL-2 or the target cell HT2. The other experiments described above prove that S4B6 actually recognizes mouse IL-2. Since HT2 can be stimulated by human or rat IL-2 even in the presence of the antibody, it is unlikely that the antibody acts on the HT2 cells. In addition, the removal of IL-2 by passage through a column containing bound S4B6 antibody indicates that the antibody binds directly to IL-2. Finally, the Western blots of IL-2 expressed in E. coli also demonstrate that the monoclonal antibody binds directly to mouse IL-2.

Some information about the specificity of S4B6 can be inferred from the data. Since the antigenic determinant is present on IL-2 synthesised in E. coli, the determinant is probably due to the polypeptide sequence, as E. coli does not glycosylate proteins. In addition, the antibody does not recognize IL-2 from rat or human, indicating that the determinant is due to a unique mouse IL-2 sequence. Such a determinant could be, e.g., the stretch of twelve glutamines found in mouse but not human IL-2.

From the foregoing, it will be appreciated that the hybridomas of the present invention produce monoclonal antibodies specific for mouse IL-2 but which are not specific for IL-2 from other sources (e.g., human and rat). The invention also provides a method for producing significant quantities of the monoclonal antibodies useful to those skilled in the art in the purification of murine IL-2, various animal studies, and generally enhancing experimental research capabilities.

I claim:

1. A hybridoma having the identifying characteristics of the cell line deposited under American Type Culture Collection accession number HB8794.

2. A monoclonal antibody produced by a hybridoma having the identifying characteristics of the cell line deposited under American Type Culture Collection accession number HB8794.

* * * * *